United States Patent [19]

Grisar et al.

[11] 3,983,248

[45] Sept. 28, 1976

[54] BIS(AMINOALKYLSULFAMOYL)AN-THRAQUINONE ANTIVIRAL AGENTS

[75] Inventors: Johann M. Grisar; Arthur D. Sill; Robert W. Fleming, all of Cincinnati, Ohio

[73] Assignee: Richardson-Merrell Inc., Wilton, Conn.

[22] Filed: Aug. 6, 1971

[21] Appl. No.: 169,861

Related U.S. Application Data

[62] Division of Ser. No. 777,885, Nov. 21, 1968, Pat. No. 3,627,791.

[52] U.S. Cl. .................................. 424/321
[51] Int. Cl.² ............................... H61K 31/18
[58] Field of Search .......................... 424/321

[56] References Cited
UNITED STATES PATENTS
2,371,101   3/1945   Kienle et al. ..................... 260/371

OTHER PUBLICATIONS

Andrewes, Viruses of Vertebrates, Williams and Wilkins Co., Balto. Md., 1964, pp. 171–180.
Feldman et al., as cited in Chem. Abstracts 59, 11312 (1963).
Cecil, A Textbook of Medicine, Ninth Edition, W. B. Saunders Co., Philadelphia, Pa. 1958, p. 1.

*Primary Examiner*—Jerome D. Goldberg
*Attorney, Agent, or Firm*—George W. Rauchfuss, Jr.; Eugene O. Retter

[57] ABSTRACT

Compounds useful as antiviral agents are those of the formula

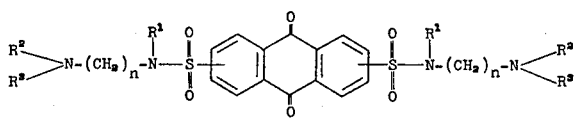

Formula I wherein each $R^1$ is hydrogen or methyl; each $n$ is an integer of 2 to 4; each of $R^2$ and $R^3$ is alkyl of 3 to 5 carbon atoms or alkenyl of 3 to 5 carbon atoms; or a pharmaceutically acceptable acid addition salt of said base. Pharmaceutical compositions are formed from these compounds with pharmaceutically acceptable carriers.

10 Claims, No Drawings

BIS(AMINOALKYLSULFAMOYL)ANTHRAQUINONE ANTIVIRAL AGENTS

This application is a division of application Ser. No. 777,885 filed Nov. 21, 1968, now U.S. Pat. No. 3,627,791, issued Dec. 14, 1971.

This invention relates to novel anthraquinone compounds. More particularly this invention relates to certain novel bis(dialkylaminoalkylsulfamoyl)anthraquinone bases, pharmaceutically acceptable acid addition salts of such bases, their method of preparation and use and pharmaceutical compositions prepared therefrom. The novel anthraquinone compounds are those of the formula

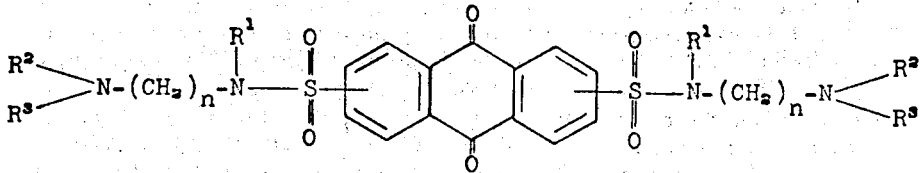

Formula I wherein each $R^1$ is hydrogen or methyl; each $n$ is an integer of 2 to 4; each of $R^2$ and $R^3$ is alkyl of 3 to 5 carbon atoms or alkenyl of 3 to 5 carbon atoms; or a pharmaceutically acceptable acid addition salt of said base.

It can be seen from the above generic Formula I that $R^1$ can be hydrogen or methyl. Preferably $R^1$ is hydrogen. Each of $R^2$ and $R^3$ is a saturated or unsaturated alkyl group having 3 to 5 carbon atoms, e.g., propyl, butyl, amyl, iso-amyl or allyl. Preferably each of $R^2$ and $R^3$ is butyl. The unsaturated alkyl is also referred to herein as alkenyl. The designator $n$ is an integer of 2 to 4 so that the ($-CH_2-$) group is 1,2-ethylene, 1,3-propylene or 1,4-butylene. Preferably $(n)$ is 3 so that the alkylene group is 1,3-propylene. The two dialkylaminoalkylsulfamoyl or dialkenylaminoalkylsulfamoyl substituents can be attached, one to each benzene ring of the anthraquinone moiety, at any positions, preferably at the 2,6- or 2,7-positions, respectively, that is, in m- or p-position in respect to the two carbonyl functions. The various $(n)$, $R^1$, $R^2$ and $R^3$ groups can be the same or different for each compound. Preferably, each $(n)$ is the same, each $R^1$ is the same and both the $R^2$ groups and $R^3$ groups are the same for any particular compound.

The closest prior art compound known to applicants is 1,5-bis[N-(4-diethylamino-1-methylbutyl)sulfamoyl]-anthraquinone. The preparation of this compound is disclosed in I. Kh. Fel'dman, Z. Ovsyanaya, and E. Kozlov, Tr. Leningr. Khim.-Farmatsevt. Inst. 1960 (11), 48–53; CA 59: 11312. However, applicants prepared and tested this compound and found that it is very much more toxic than the compounds of this invention. Furthermore, this compound was found to be inactive in antiviral tests used with the compounds of this invention.

Salts of the base compounds of this invention are primarily pharmaceutically acceptable acid addition salts with inorganic or organic acids. Suitable inorganic acids are, for example, mineral acids, such as hydrohalic acids, e.g., hydrochloric or hydrobromic acid, or sulfuric or phosphoric acids. Organic acids are, for example, lower aliphatic hydrocarbon monocarboxylic acids, e.g., glycolic or lactic acid and the like, lower aliphatic lower alkoxyhydrocarbon monocarboxylic acids, e.g., methoxy-acetic or ethoxy-acetic acids and the like, lower aliphatic lower alkanoyl-hydrocarbon monocarboxylic acids, e.g., pyruvic acid and the like, lower aliphatic hydrocarbon dicarboxylic acids, e.g., oxalic, malonic, succinic, methylsuccinic, dimethylsuccinic, glutaric, α-methylglutaric, β-methylglutaric, itaconic, maleic, citraconic, homocitraconic, or fumaric acid and the like, lower aliphatic hydroxy-hydrocarbon dicarboxylic acids, e.g., malic or tartaric acid and the like, lower aliphatic lower alkoxy-hydrocarbon dicarboxylic acids, e.g., α,β-dimethoxysuccinic or ethoxymaleic acid and the like, lower aliphatic hydrocarbon tricarboxylic acids, e.g., aconitic or tricarballylic acid and the like, lower aliphatic hydroxy-hydrocarbon tricarboxylic acids, e.g., citric acid and the like. Furthermore, organic sulfonic acids, such as lower alkane sulfonic acids, e.g., methane sulfonic or ethane sulfonic acid and the like, or lower hydroxy-alkane sulfonic acids, e.g., 2-hydroxy-ethane sulfonic acid and the like, may be suitable. Particularly useful are pharmacologically acceptable acid addition salts with mineral acids, e.g., hydrochloric acid. Mono- or di-acid salts may be formed; also, the salts can be hydrated, e.g., monohydrate, or substantially anhydrous.

The compounds of this invention can be administered to animals, e.g., warm-blooded animals, for their prophylactic and/or therapeutic antiviral effects by conventional modes of administration, either alone but preferably with pharmaceutical carriers. Illustratively, administration can be parenterally, e.g., subcutaneously or intramuscularly, topically, e.g., intranasally or intravaginally, or orally.

The dosage administered will be dependent upon the virus for which treatment or prophylaxis is desired, the type of animal involved, and similar considerations. Generally, a daily dosage of the active ingredient can be from less than about 0.02 to over 500 mg. (milligram) per kg. (kilogram) of body weight and preferably from about 0.1 to about 50 mg/kg of body weight. The novel compounds together with conventional pharmaceutical carriers can be employed in unit dosage forms such as solids, for example, tablets or capsules, or liquid solutions, suspensions, or elixirs for oral administration and ingestion or liquid solutions, suspensions, emulsions and the like for parenteral use. The quantity of active ingredient in each dosage will generally differ depending on the type of unit dosage, the type of animal and its weight. Thus, each dosage can contain from less than about 0.1 mg. to over 250 mg. of active ingredient in a significant quantity of pharmaceutical carrier.

The compounds of this invention can be used as antiviral agents for inhibiting or preventing a variety of viral diseases or infections. Illustratively, the compounds can be used for their antiviral effect against diseases caused or associated with picornavirus types, myxoviruses, arboviruses, poxviruses, and the like. When administered prophylactically, it is preferred that the administration of the compound be within 24 or 48 hours prior to invasion of the animal with pathogenic virus. When administered therapeutically, it is preferred that the administration be within about 24 or 48 hours after invasion with pathogenic virus. Preferably, these compounds are administered to the animal both prior, i.e., prophylactically, and after invasion, i.e., therapeutically, of the animal with a pathogenic virus, e.g., by administration of the compound on the day of invasion as well as for a day or two prior to invasion and a day or two after such invasion.

The compounds of this invention have a tendency to degrade or react in contact with metals, e.g., galvanized steel. Therefore, it is preferred that metals which come in contact with these compounds be resistant to corrosion. A metal which can be used in contact with these compounds is stainless steel.

A preferred mode of administration for the compounds (active ingredients) of this invention is parenterally such as by normally liquid injectable compositions, e.g., for intramuscular or subcutaneous administration. In such compositions the quantity of active ingredient can vary from about 0.05 to 20% by weight of the composition and preferably from about 0.1 to 10% by weight. In order to minimize or eliminate irritation at the site of injection, the parenteral compositions can contain a nonionic surfactant such as those having an HLB (hydrophilelipophile balance) of about 12 to 17. Such formulations can be solutions, suspensions or emulsions in conventional liquid pharmaceutical carriers, e.g., sterile liquids such as water, saline, and aqueous dextrose (glucose) and related sugar solutions. The quantity of surfactant in the formulation can vary from about 5 to 15% by weight of the formulation. The quantity of a compound of this invention, either in the base form or a pharmaceutically acceptable acid addition salt in such formulations, can vary over a broad range such as that mentioned hereinbefore, i.e., 0.5 to 20% by weight of the formulation. Preferably, the active ingredient is in the base form. The remaining component or components of such formulations can be a normally liquid pharmaceutical carrier, e.g., isotonic aqueous saline, either alone or together with conventional excipients for injectable compositions. The surfactant can be a single surfactant having the above indicated HLB or a mixture of two or more surfactants wherein such mixture has the indicated HLB. The following surfactants are illustrative of those which can be used in such formulations: (A) Polyoxyethylene derivatives of sorbitan fatty acid esters, such as the TWEEN series of surfactants, e.g., TWEEN 80, and the like. The TWEENS are manufactured by Atlas Powder Company. (B) High molecular weight adducts of ethylene oxide with a hydrophobic base formed by the condensation of propylene oxide with propylene glycol, e.g., PLURONIC F-68 which is manufactured by Wyandotte Chemical Company. The preferred surfactant is Polysorbate 80, U.S.P., a polyoxyethylene sorbitan monooleate.

The compounds of the present invention can be prepared by reaction of an anthraquinonedisulfonyl (lower) alkyl ester or halide, e.g., chloride or bromide dissolved or suspended in an inert solvent such as methylene chloride, with an excess of the appropriately substituted diamine over periods of from 1 hour to 7 days at temperatures ranging from room temperature to reflux of solvent. The term (lower) as used to describe alkyl relates to alkyls having from 1 to 6 carbon atoms, e.g., ethyl. This reaction is illustrated by the following equation:

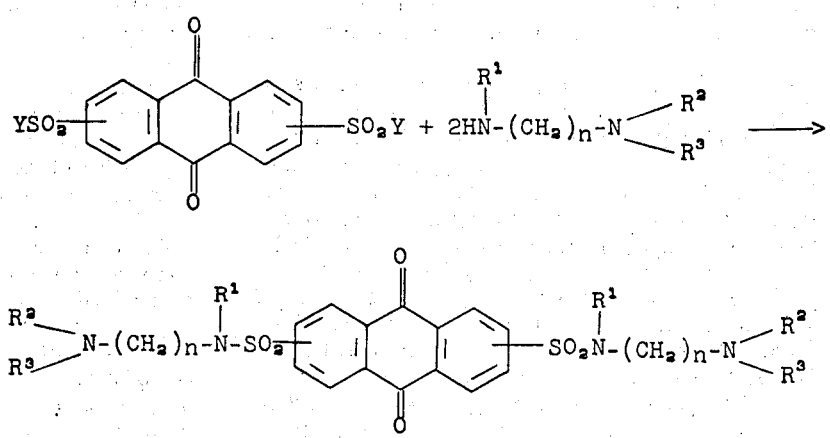

wherein Y is a halide or (lower) alkoxy and $R^1$, $R^2$, $R^3$ and $(n)$ have the same meaning as in Formula I.

The product can be isolated in some cases directly from the reaction mixture and purified by recrystallization. In other cases, the product was isolated as the free base after removal of excess starting material by appropriate washes.

Alternatively, the compounds of this invention may be prepared by alkylation of the Na, K or Li derivatives of N,N'-dimethyl anthraquinonedisulfonamides with dialkylaminoalkyl halides, or the N,N'-bis(dialkylaminoalkyl)anthraquinonesulfonamides may be alkylated with methylating agents such as methyl halide or a reactive ester of methanol such as methyl sulfate or methyl p-toluenesulfonate.

The anthraquinonedisulfonyl chloride intermediates can be prepared from the disulfonic acids or their salts by a variety of procedures well known to the art and described in detail by H. E. Fierz-David in *Helvetica Chimica Acta*, Volume 10, pages 197 to 227 (1927).

The following examples are illustrative of the invention.

EXAMPLE 1

PREPARATION OF 2,6-BIS-[N-(3-DIBUTYLMINOPROPYL)SULFAMOYL]ANTHRAQUINONE DIHYDROCHLORIDE

To a suspension of 40.5 grams (0.1 mole) of anthraquinone-2,6-disulfonyl chloride in 500 ml. of dry methylene chloride was added dropwise over 3 hours a solution of 46.6 g. (0.25 mole) of 3-dibutylaminopropylamine in 250 ml. of methylene chloride, and the mixture was stirred overnight at room temperature. The resulting precipitate was collected, washed with methylene chloride and recrystallized twice from a mixture of methanol and butanone adjusted, by boiling off methanol, to a proportion of the two solvents most conducive to crystallization. The product, m.p. 185°–186°, was obtained in a yield, after recovery of a second crop, of 75%.

EXAMPLE 2

PREPARATION OF OTHER 2,6-BIS-[N-(DIALKYLAMINOALKYL)SULFAMOYL]ANTHRAQUINONE COMPOUNDS

Using the procedure described in Example 1, additional 2,6-bis-[N-(dialkylaminoalkyl)sulfamoyl]anthraquinone derivatives were prepared. The base form of such compounds is shown by the following formula wherein the designator A is described in the below Table I.

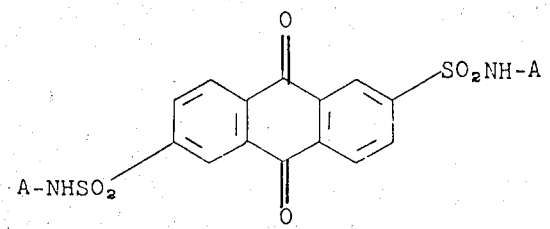

TABLE I

| A | Melting Point | Molecular Formula |
|---|---|---|
| $(CH_2)_3-N[CH_2CH_2CH(CH_3)_2]_2$ | 199–200°C. | $C_{40}H_{64}N_4O_6S_2.2HCl$ |
| $(CH_2)_4-N(C_4H_9-n)_2$ | 155–156°C. | $C_{38}H_{60}N_4O_6S_2$ |
| $(CH_2)_2-N(C_4H_9-n)_2$ | 165–166°C. | $C_{34}H_{52}N_4O_6S_2$ |
| $(CH_2)_3-N(CH_2CH=CH_2)_2$ | 147–149°C. | $C_{32}H_{40}N_4O_6S_2.2C_4H_4O_4$[a] |
| $(CH_2)_3-N(C_3H_7-n)_2$ | 234–235°C. | $C_{32}H_{48}N_4O_6S_2.2HCl$ |
| $(CH_2)_3-N(C_5H_{11}-n)_2$ | 191–192°C. | $C_{40}H_{64}N_4O_6S_2.2HCl$ |

[a]Diacid maleate salt

EXAMPLE 3

PREPARATION OF 2,7-BIS-[N-(3-DIBUTYLAMINOPROPYL)SULFAMOYL]ANTHRAQUINONE

Following the procedure of Example 1 and using anthraquinone-2,7-disulfonyl chloride, the title compound was obtained. Since the dihydrochloride was hygroscopic, it was converted to the free base by stirring it in a 10% sodium carbonate solution and recrystallized from a mixture of ether and hexane, m.p. 93°–95°.

EXAMPLE 4

PREPARATION OF ISOMERIC BIS-[N-(3-DIBUTYLAMINOPROPYL)SULFAMOYL]ANTHRAQUINONES

Similarly, following the procedure of Example 1 and using the appropriate anthraquinonedisulfonyl chlorides, were prepared, the 1,5-isomer, m.p. 132°–133° (as free base) or 203°–204° (as diacid maleate), the 1,8-isomer, m.p. 176°–8° (as dihydrochloride), the 1,6-isomer, m.p. 57°–60° (as diacid maleate). The 1,7-isomer can similarly be prepared from the known anthraquinone-1,7-disulfonyl chloride.

EXAMPLE 5

PREPARATION OF 2,6-BIS-[N-(3-DIBUTYLAMINOPROPYL)-N-METHYLSULFAMOYL]ANTHRAQUINONE

Following the procedure of Example 1 and using N-methyl-N',N'-dibutylpropylenediamine, the title compound can be prepared.

Examples 6 to 22 illustrate in vivo antiviral studies with compounds, also referred to as active ingredients, of this invention. In each of the examples, the compounds were antivirally active. In Examples 7–22, the compounds showed antiviral activity by prolonging the mean day of death of the treated animals as compared to the control animals, during the period of observation. In Example 6, antiviral activity was shown by fewer lesions for the treated animals as compared to the controls, during the period of observation. The dosage levels of the compounds used in the examples were within the range of 2 to 50 mg. per kg. of animal body weight for each time the compound was administered.

Table A lists the active ingredient which was administered in each of the examples. Although it is believed that the headings in the examples are self-explanatory, some of the headings are explained as follows: The "challenge", i.e., inoculation with a virus, used is generally fatal to all the untreated, i.e., control, animals in the experiment. "Time of death" refers to the average time of death for the untreated animals. The "Treatment" was prophylactic or therapeutic or both. The term "volume" refers to the volume of composition administered per dose which contained the active ingredient dissolved in sterile water which also contained 0.15% of hydroxyethylcellulose. The control animals received a sham dosage of the same volume of the vehicle which did not contain the active ingredient.

TABLE A

| Example | Compound |
|---|---|
| 6 and 7 | 2,7-Bis-[N-(3-dibutylaminopropyl)sulfamoyl]-anthraquinone |
| 8 | 2,7-Bis-[N-(3-dibutylaminopropyl)sulfamoyl]-anthraquinone diacid maleate |

TABLE A-continued

| Example | Compound |
|---------|----------|
| 9 to 14 | 2,6-Bis-[N-(3-dibutylaminopropyl)sulfamoyl]-anthraquinone dihydrochloride |
| 15 | 1,8-Bis-[N-(3-dibutylaminopropyl)sulfamoyl]-anthraquinone dihydrochloride |
| 16 | 1,5-Bis-[N-(3-dibutylaminopropyl)sulfamoyl]-anthraquinone |
| 17 | 1,6-Bis-[N-(3-dibutylaminopropyl)sulfamoyl]-anthraquinone diacid maleate |
| 18 | 2,6-Bis-[N-(3-diisopentylaminopropyl)-sulfamoyl]anthraquinone dihydrochloride |
| 19 | 2,6-Bis-[N-(2-dibutylaminoethyl)sulfamoyl]-anthraquinone |
| 20 | 2,6-Bis-[N-(3-diallylaminopropyl)sulfamoyl]-anthraquinone diacid maleate |
| 21 | 2,6-Bis-[N-(3-dipropylaminopropyl)sulfamoyl]-anthraquinone dihydrochloride |
| 22 | 2,6-Bis-[N-(3-dipentylaminopropyl)sulfamoyl]-anthraquinone dihydrochloride |

| EXAMPLE | 6 | 7 | 8 | |
|---|---|---|---|---|
| VIRUS | Vaccinia IHD | Encephalomyocarditis | Encephalomyocarditis | |
| type | DNA, Poxvirus | RNA, Picornavirus | RNA, Picornavirus | |
| challenge | 24 $ID_{50}$ | 20 $LD_{50}$ | 15 $LD_{50}$ | |
| route | subcutaneous in tail | subcutaneous | subcutaneous | |
| time of death | tail lesion scored | 5 days | 5 days | |
| period of observation | on 7th day | 10 days | 10 days | |
| ANIMAL | mice | mice | mice | |
| weight | 18–20 grams | 12–15 grams | 12–15 grams | |
| treated group | 10 | 10 | 10 | |
| control group | 20 | 30 | 40 | |
| TREATMENT | Prophylactic and Therapeutic | Prophylactic and Therapeutic | Prophylactic and Therapeutic | |
| route | subcutaneous | subcutaneous | subcutaneous | |
| volume | 0.25 ml. | 0.25 ml. | 0.25 ml. | |
| time pre-challenge | 28, 22, 4 hrs. | 28, 22, 4 hrs. | 28, 22, 4 hrs. | |
| post-challenge | 2, 20, 26 hrs. | 2, 20, 26 hrs. | 2, 20, 26 hrs. | |
| EXAMPLE | 9 | 10 | 11 | 12 |
| VIRUS | Encephalomyocarditis | Influenza $A_0(PR_8)$ | Influenza A/Equine (Prague) | Mengo |
| type | RNA, Picornavirus | RNA, Myxovirus | RNA, Myxovirus | RNA, Picornavirus |
| challenge | 15 $LD_{50}$ | 16 $LD_{50}$ | 68 $LD_{50}$ | 10 $LD_{50}$ |
| route | subcutaneous | intranasal | intranasal | subcutaneous |
| time of death | 5 days | 5 days | 5 days | 5 days |
| period of observation | 10 days | 10 days | 10 days | 10 days |
| ANIMAL | mice | mice | mice | mice |
| weight | 12–15 grams | 12–15 grams | 12–15 grams | 12–15 grams |
| treated group | 10 | 10 | 5 | 10 |
| control group | 40 | 29 | 5 | 20 |
| TREATMENT | Prophylactic and Therapeutic | Prophylactic and Therapeutic | Prophylactic and Therapeutic | Prophylactic and Therapeutic |
| route | subcutaneous | intraperitoneal | subcutaneous | subcutaneous |
| volume | 0.25 ml. | 0.25 ml. | 0.25 ml. | 0.25 ml. |
| time pre-challenge | 28, 22, 4 hrs. | 1 hr. | 28, 22, 4 hrs. | 28, 22, 4 hrs. |
| post-challenge | 2, 20, 26 hrs. | 3, 6, 24, 27 hrs. | 2, 20, 26 hrs. | 2, 20, 26 hrs. |
| EXAMPLE | 13 | 14 | 15 | 16 |
| VIRUS | Semliki Forest | Vaccinia IHD | Encephalomyocarditis | Encephalomyocarditis |
| type | RNA, Arbovirus | DNA, Poxvirus | RNA, Picornavirus | RNA, Picornavirus |
| challenge | 31 $LD_{50}$ | 240 $ID_{50}$ | 10 $LD_{50}$ | 15 $LD_{50}$ |
| route | subcutaneous | subcutaneous in tail | subcutaneous | subcutaneous |
| time of death | 5 days | tail lesion scored | 5 days | 5 days |
| period of observation | 10 days | on 7th day | 10 days | 10 days |
| ANIMAL | mice | mice | mice | mice |
| weight | 12–15 grams | 12–15 grams | 12–15 grams | 12–15 grams |
| treated group | 10 | 10 | 10 | 10 |
| control group | 20 | 20 | 10 | 30 |
| TREATMENT | Prophylactic and Therapeutic | Prophylactic and Therapeutic | Prophylactic and Therapeutic | Prophylactic and Therapeutic |
| route | subcutaneous | subcutaneous | subcutaneous | subcutaneous |
| volume | 0.25 ml. | 0.25 ml. | 0.25 ml. | 0.25 ml. |
| time pre-challenge | 28, 22, 4 hrs. | 28, 22, 4 hrs. | 28, 22, 4 hrs. | 28, 22, 4 hrs. |
| post-challenge | 2, 20, 26 hrs. | 2, 20, 26 hrs. | 2, 20, 26 hrs. | 2, 20, 26 hrs. |
| EXAMPLE | 17 | 18 | 19 | |
| VIRUS | Encephalomyocarditis | Encephalomyocarditis | Encephalomyocarditis | |
| type | RNA, Picornavirus | RNA, Picornavirus | RNA, Picornavirus | |
| challenge | 15 $LD_{50}$ | 13 $LD_{50}$ | 13 $LD_{50}$ | |
| route | subcutaneous | subcutaneous | subcutaneous | |
| time of death | 5 days | 5 days | 5 days | |
| period of observation | 10 days | 10 days | 9 days | |
| ANIMAL | mice | mice | mice | |
| weight | 12–15 grams | 12–15 grams | 12–15 grams | |
| treated group | 10 | 10 | 10 | |
| control group | 30 | 30 | 20 | |
| TREATMENT | Prophylactic and Therapeutic | Prophylactic and Therapeutic | Prophylactic and Therapeutic | |
| route | subcutaneous | subcutaneous | subcutaneous | |
| volume | 0.25 ml. | 0.25 ml. | 0.25 ml. | |
| time pre-challenge | 28, 22, 4 hrs. | 28, 22, 4 hrs. | 28, 22, 2 hrs. | |
| post-challenge | 2, 20, 26 hrs. | 2, 20, 26 hrs. | 2, 20, 26 hrs. | |
| EXAMPLE | 20 | 21 | 22 | |
| VIRUS | Encephalomyocarditis | Encephalomyocarditis | Encephalomyocarditis | |
| type | RNA, Picornavirus | RNA, Picornavirus | RNA, Picornavirus | |
| challenge | 13 $LD_{50}$ | 10 $LD_{50}$ | 10 $LD_{50}$ | |

| route | subcutaneous | subcutaneous | subcutaneous |
|---|---|---|---|
| time of death | 5 days | 5 days | 5 days |
| period of observation | 9 days | 9 days | 9 days |
| ANIMAL | mice | mice | mice |
| weight | 12–15 grams | 12–15 grams | 12–15 grams |
| treated group | 10 | 10 | 10 |
| control group | 20 | 10 | 20 |
| TREATMENT | Prophylactic and Therapeutic | Prophylactic and Therapeutic | Prophylactic and Therapeutic |
| route | subcutaneous | subcutaneous | subcutaneous |
| volume | 0.25 ml. | 0.25 ml. | 0.25 ml. |
| time pre-challenge | 28, 22, 2 hrs. | 28, 22, 2 hrs. | 28, 22, 2 hrs. |
| post-challenge | 2, 20, 26 hrs. | 2, 20, 26 hrs. | 2, 20, 26 hrs. |

EXAMPLE 23

An illustrative composition for a parenteral injection is the following wherein the quantities are on a weight of volume basis.

| | |
|---|---|
| (a) 2,6-Bis-[N-(3-dibutylaminopropyl)sulfamoyl]-anthraquinone dihydrochloride | 100 mg. |
| (b) Sodium chloride | q.s. |
| (c) Water for injection to make | 10 ml. |

The composition is prepared by dissolving the active ingredient and sufficient sodium chloride in water for injection to render the solution isotonic. The composition may be dispensed in a single ampule containing 100 mg. of the active ingredient for multiple dosage or in 10 ampules for single dosage.

EXAMPLE 24

An illustrative composition for a parenteral injection is the following aqueous emulsion.

| Each ml.(milliliter) contains | Ingredient | Amount |
|---|---|---|
| 2.5 mg. | 2,6-Bis-[N-(3-dibutyl-aminopropyl)sulfamoyl]anthraquinone | 0.050 g. |
| 100 mg. | Polysorbate 80 | 2.000 g. |
| 0.0064 mg. | Sodium chloride | 0.128 g. |
| — | Water for injection,q.s. | 20.000 ml. |

The composition of Example 24 is prepared by: dissolving 0.64 grams of sodium chloride in 100 ml. of water for injection; mixing the Polysorbate 80 with the active ingredient; adding a sufficient solution of the sodium chloride in water to the active ingredient and Polysorbate to make 20 ml.; shaking the mixture; and then autoclaving it for 20 minutes at 110°C. at 15 p.s.i.g. steam pressure. The composition can be dispensed in a single ampule for multiple dosage or in 10 or 20 ampules for single dosages.

We claim:

1. A pharmaceutical composition, in unit dosage form, comprising from about 0.1 to 250 milligrams of a bis(aminoalkylsulfamoyl)anthraquinone and a significant quantity of a pharmaceutical carrier, said anthraquinone selected from a base of the formula:

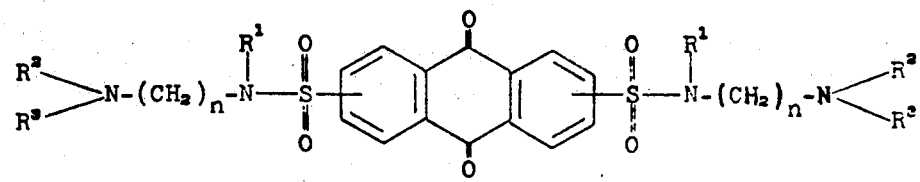

wherein each $R^1$ is hydrogen or methyl; each $n$ is an integer of 2 to 4; each of $R^2$ and $R^3$ is alkyl of 3 to 5 carbon atoms or alkenyl of 3 to 5 carbon atoms; or a pharmaceutically acceptable acid addition salt of said base.

2. A composition of claim 1 wherein the anthraquinone is 2,6-bis[N-(3-dibutylaminopropyl)sulfamoyl]anthraquinone or a pharmaceutically acceptable acid addition salt thereof.

3. A composition of claim 1 wherein the anthraquinone is 2,7-bis[N-(3-dibutylaminopropyl)sulfamoyl]anthraquinone or a pharmaceutically acceptable acid addition salt thereof.

4. A normally liquid parenterally administrable pharmaceutical composition comprising from about 5 to 15%, by weight, of a non-ionic surfactant having an HLB of from about 12 to 17; a significant quantity of a normally liquid pharmaceutical carrier; and from about 0.05 to 20% by weight of an anthraquinone selected from a base of the formula

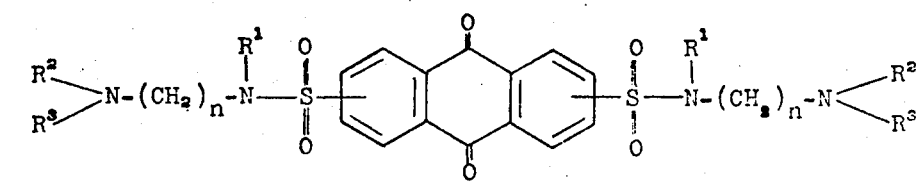

wherein each $R^1$ is hydrogen or methyl; each $n$ is an integer of 2 to 4; each of $R^2$ and $R^3$ is alkyl of 3 to 5 carbon atoms or alkenyl of 3 to 5 carbon atoms; or a pharmaceutically acceptable acid addition salt of said base.

5. A composition of claim 4 wherein the anthraquinone is in the base form.

6. A composition of claim 4 wherein the anthraquinone is 2,6-bis[N-(3-dibutylaminopropyl)sulfamoyl]anthraquinone or a pharmaceutically acceptable acid addition salt thereof.

7. A composition of claim 4 wherein the anthraquinone is 2,7-bis[N-(3-dibutylaminopropyl)sulfamoyl]anthraquinone or a pharmaceutically acceptable acid addition salt thereof.

8. A method for prophylaxis and treatment of a viral infection, which comprises administering to a warm-blooded animal an antivirally effective quantity of a compound selected from a base of the formula:

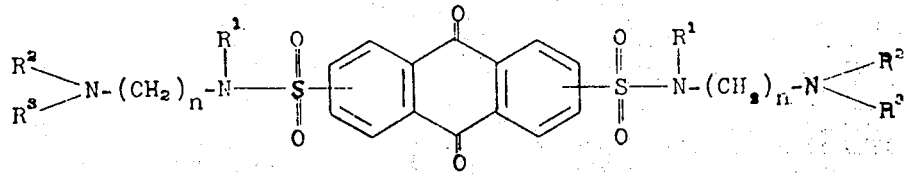

wherein each $R^1$ is hydrogen or methyl; each $n$ is an integer of 2 to 4; each of $R^2$ and $R^3$ is alkyl of 3 to 5 carbon atoms or alkenyl of 3 to 5 carbon atoms; or a pharmaceutically acceptable acid addition salt of said base.

9. A method of claim 8 wherein the anthraquinone is 2,6-bis[N-(3-dibutylaminopropyl)sulfamoyl]anthraquinone or a pharmaceutically acceptable acid addition salt thereof.

10. A method of claim 8 wherein the anthraquinone is 2,7-bis[N-(3-dibutylaminopropyl)sulfamoyl]anthraquinone or a pharmaceutically acceptable acid addition salt thereof.

* * * * *

UNITED STATES PATENT AND TRADEMARK OFFICE
CERTIFICATE OF CORRECTION

PATENT NO. : 3,983,248

DATED : September 28, 1976

INVENTOR(S) : Johann M. Grisar, Arthur D. Sill and Robert W. Fleming

It is certified that error appears in the above-identified patent and that said Letters Patent are hereby corrected as shown below:

Column 3, line 60, "i.e. 0.5 to 20%" should read "i.e. 0.05 to 20%". Column 9, line 19, "of volume basis" should read "to volume basis".

Signed and Sealed this

Twenty-first Day of March 1978

[SEAL]

Attest:

RUTH C. MASON
Attesting Officer

LUTRELLE F. PARKER
Acting Commissioner of Patents and Trademarks